United States Patent
Kim et al.

(10) Patent No.: US 12,383,417 B2
(45) Date of Patent: Aug. 12, 2025

(54) KNEE JOINT GUIDE APPARATUS

(71) Applicant: Seoul National University R&DB Foundation, Seoul (KR)

(72) Inventors: Yoon Young Kim, Seoul (KR); Jeonghan Yu, Seoul (KR); Seok Won Kang, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 533 days.

(21) Appl. No.: 17/896,052

(22) Filed: Aug. 25, 2022

(65) Prior Publication Data
US 2023/0073133 A1    Mar. 9, 2023

(30) Foreign Application Priority Data
Aug. 26, 2021  (KR) .......................... 10-2021-0113279

(51) Int. Cl.
*A61F 5/01*  (2006.01)

(52) U.S. Cl.
CPC .... *A61F 5/0123* (2013.01); *A61F 2005/0144* (2013.01)

(58) Field of Classification Search
CPC ...... A61F 2005/0144; A61F 2005/0155; A61F 2/64; A61F 2/68; A61F 2/70; A61F 2/50; A61F 2/642; A61F 2/644; A61F 2002/5007; A61F 2002/701; A61F 2002/30471; A61F 2002/5087; A61F 2002/5009; A61F 2002/5003; A61H 3/00; A61H 1/02
USPC .......................................................... 602/16
See application file for complete search history.

(56) References Cited

FOREIGN PATENT DOCUMENTS

| | | | |
|---|---|---|---|
| JP | 2008278921 | 11/2008 | |
| JP | 2013150714 | 8/2013 | |
| KR | 1020100134943 | 12/2010 | |
| KR | 101430307 B1 | 8/2014 | |
| KR | 101948261 | 2/2019 | |
| KR | 102032500 | 11/2019 | |
| KR | 102032500 B1 * | 11/2019 | ............... A61H 3/00 |
| KR | 20200011074 A | 2/2020 | |
| KR | 1020210154690 | 12/2021 | |

OTHER PUBLICATIONS

June et al., Translation of KR 102032500 B1, 2019 (Year: 2019).*

* cited by examiner

*Primary Examiner* — Alireza Nia
*Assistant Examiner* — Daniel A Miller
(74) *Attorney, Agent, or Firm* — CANTOR COLBURN LLP

(57) ABSTRACT

Disclosed is a knee joint guide apparatus which can be driven even at any point on a plane in which an instantaneous rotation center of a knee joint can be positioned by a self-alignment function, and can also implement output performance required for a walking operation through a mechanical advantage change depending on a flexion angle. The knee joint guide apparatus includes: a proximal body link provided above a knee joint; a distal body link provided at a location corresponding to the proximal body link below the knee joint; and a planar rigid body 6-bar linkage mechanism including a plurality of revolute joints and a plurality of prismatic joints, and a plurality of links between the proximal body link and the distal body link to output a mechanical advantage depending on a flexion angle of the knee joint in movement of the knee joint with a self-alignment function.

10 Claims, 9 Drawing Sheets

KNEE JOINT GUIDE APPARATUS

CROSS-REFERENCE TO RELATED APPLICATION

This application claims priority to and the benefit of Korean Patent Application No. 10-2021-0113279 filed in the Korean Intellectual Property Office on Aug. 26, 2021, the entire contents of which are incorporated herein by reference.

BACKGROUND OF THE INVENTION

(a) Field of the Invention

The present disclosure relates to a knee joint guide apparatus.

(b) Description of the Related Art

Depending on a knee joint shape of a wearer, an instantaneous center of rotation path of a knee joint changes upon walking. A conventional knee joint mechanism is difficult to be applied to multiple people as it is formed by a simple revolute joint or simulates only a representative instantaneous center of rotation path.

In recent years, a knee mechanism joint with its self-alignment function has been designed in consideration of the knee joint instantaneous center of rotation path of various wearers, but due to the increase in degrees of freedom, power and speed transmission characteristics are not easy for walking. In addition, in order to use a wearable robot without causing a strain on a body of the wearer, a robot design according to an individual body type and a manual wearing process of an expert are required, but it is difficult to commercialize the wearing robot due to high cost.

The above information disclosed in this Background section is only for enhancement of understanding of the background of the disclosure, and therefore it may contain information that does not form the prior art that is already known in this country to a person of ordinary skill in the art.

SUMMARY OF THE INVENTION

The present disclosure has been made in an effort to provide a knee joint guide apparatus which can be driven even at any point on a plane in which an instantaneous rotation center of a knee joint can be positioned by a self-alignment function, and can also implement output performance required for a walking operation through a mechanical advantage change depending on a flexion angle.

An exemplary embodiment of the present disclosure provides a knee joint guide apparatus which includes: a proximal body link provided above a knee joint, a distal body link provided at a location corresponding to the proximal body link below the knee joint, and a planar rigid body 6-bar linkage mechanism including a plurality of revolute joints and a plurality of prismatic joints, and a plurality of links to output a mechanical advantage depending on a flexion angle of the knee joint in movement of the knee joint with a self-alignment function.

The knee joint and the proximal body link, the distal body link, and the planar rigid body 6-bar linkage mechanism may form one closed loop and have one degree of freedom.

The planar rigid body 6-bar linkage mechanism may include three revolute joints, three prismatic joints, and four links.

Three revolute joints may include a first revolute joint connecting the proximal body link and a first link, a second revolute joint connecting the first link and a second link, and a third revolute joint connecting the proximal body link and a third link.

Three prismatic joints may include a first prismatic joint connecting the second link and the third link, a second prismatic joint connecting the third link and a fourth link, and a third prismatic joint connecting the fourth link and the distal body link.

The first prismatic joint, the third revolute joint, and the second prismatic joint may be connected to each other through the third link.

The first revolute joint is connected to one side of the proximal body link, one side of the first link is connected to the first revolute joint, the second revolute joint is connected to the other side of the first link, one side of the second link is connected to the second revolute joint, the first prismatic joint is connected to the other side of the second link, one side of the third link is connected to the first prismatic joint, and the third revolute joint is connected to the third link to form a first closed loop.

The third revolute joint is connected to the other side of the proximal body link, one side of the third link is connected to the third revolute joint, the second prismatic joint is connected to the other side of the third link, one side of the fourth link is connected to the second prismatic joint, and the third prismatic joint is connected to the other side of the fourth link to form a second closed loop.

The flexion angle of the knee joint may be set to 0 degree to 180 degrees.

The first revolute joint may further include an actuating unit generating actuating torque.

Four links may include at least one ternary link.

According to an exemplary embodiment of the present disclosure, since a knee joint guide apparatus can be used for walking operations of multiple persons without complicated customizing task even by a single product, manufacturing cost can be reduced and a wearer range can be increased.

Further, there is an effect that a new mechanism specialized in the walking operation can be implemented through a mechanical advantage change according to a knee flexion angle for any point on a plane in which an instantaneous rotation center of a knee joint can be positioned.

DETAILED DESCRIPTION OF THE EMBODIMENTS

Figure 1:
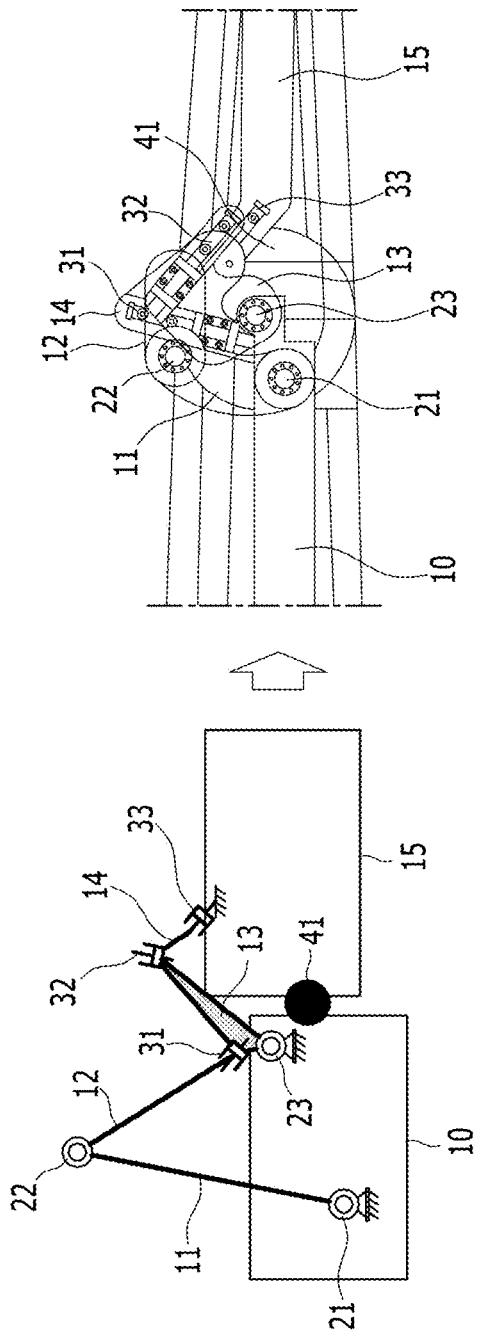
FIG. 1 is a diagram schematically illustrating a knee joint guide apparatus according to an exemplary embodiment of the present disclosure.

The terms used herein is for the purpose of describing specific exemplary embodiments only and are not intended to be limiting of the present disclosure. The singular forms used herein include plural forms as well, if the phrases do not clearly have the opposite meaning. The terms "comprises," "comprising," "includes" and/or "including" used in the specification means that a specific feature, region, integer, step, operation, element and/or component is embodied and presence or addition of other specific features, regions, integers, steps, operations, elements, components, and/or groups are not excluded.

Unless defined otherwise, all terms including technical and scientific terms used herein have the same meaning as commonly understood by those skilled in the art to which the present disclosure belongs. Commonly used predefined terms are further interpreted as having a meaning consistent with the relevant technical literature and the present disclosure, and are not construed as ideal or very formal meanings unless defined otherwise.

The present disclosure will be described more fully hereinafter with reference to the accompanying drawings, in which exemplary embodiments of the disclosure are shown. As those skilled in the art would realize, the described embodiments may be modified in various different ways, all without departing from the spirit or scope of the present disclosure.

The drawings and description are to be regarded as illustrative in nature and not restrictive. Like reference numerals designate like elements throughout the specification. In addition, some components are exaggerated or omitted or schematically illustrated in the accompanying drawings, and the size of each component does not fully reflect an actual size.

FIG. 1 is a diagram schematically illustrating a knee joint guide apparatus according to an exemplary embodiment of the present disclosure.

Referring to FIG. 1, the knee joint guide apparatus according to the exemplary embodiment includes a proximal body link 10, a distal body link 15, and a planar rigid body 6-bar linkage mechanism.

The proximal body link 10 is a part provided above a knee joint. The distal body link 15 is a part provided at a location corresponding to the proximal body link 10 below the knee joint.

The planar rigid body 6-bar linkage mechanism connects the proximal body link 10 connected to a femoral region of a wearer and the distal body link 15 connected to the shin of the wearer.

The planar rigid body 6-bar linkage mechanism may implement a self-alignment function at any point on a plane in which an instantaneous rotation center of the knee joint may be positioned, and implement output performance required for a walking operation through a mechanical advantage changes depending on a knee flexion angle in walking.

The planar rigid body 6-bar linkage mechanism is a part that includes a plurality of revolute joints and a plurality of prismatic joints, and a plurality of links between the proximal body link 10 and the distal body link 15 to output a mechanical advantage depending on the flexion angle of the knee joint in movement of the knee joint with the self-alignment function. For example, the planar rigid body 6-bar linkage mechanism may include a mutual connection structure among three revolute joints, three prismatic joints, and four links. Here, three revolute joints include a first revolute joint 21, a second revolute joint 22, and a third revolute joint 23. Three prismatic joints include a first prismatic joint 31, a second prismatic joint 32, and a third prismatic joint 33. Four links include a first link 11, a second link 12, a third link 13, and a fourth link 14.

An actuating unit may be applied to the first revolute joint 21. The proximal body link 10 and the first link 11 are connected by the first revolute joint 21. The first link 11 and the second link 12 are connected by the second revolute joint 22. The second link 12 and the third link 13 are connected by the first prismatic joint 31. The third link 13 and the proximal body link 10 are connected by the third revolute joint 23.

Further, the third link 13 and the fourth link 14 are connected by the second prismatic joint 32. The fourth link 14 and the distal body link 15 are connected by the third prismatic joint 33.

The planar rigid body 6-bar linkage mechanism including three revolute joints, three prismatic joints, and four links is a part different from a knee joint mechanism proposed in conventional robots. The planar rigid body 6-bar linkage mechanism may have the self-alignment function, and output the mechanical advantage depending on the flexion angle of the knee joint in walking.

The distal body link 15 and the proximal body link 10 may be connected through a knee joint 41 of the wearer. In this case, since the knee joint 41 has any location and any flexion angle on a plane, the knee joint 41 may be expressed with three degrees of freedom on the plane. The knee joint 41 and the proximal body link 10, the distal body link 15, and the planar rigid body 6-bar linkage mechanism may form one closed loop and have one degree of freedom.

The planar rigid body 6-bar linkage mechanism is configured to have three revolute joints and three prismatic joints as described above, and the planar rigid body 6-bar linkage mechanism may be driven even at any point on the plane in which the instantaneous rotation center of the knee joint may be positioned with the self-alignment function and show the output performance required for the walking operation through the mechanical advantage change depending on the flexion angle.

Figure 2:
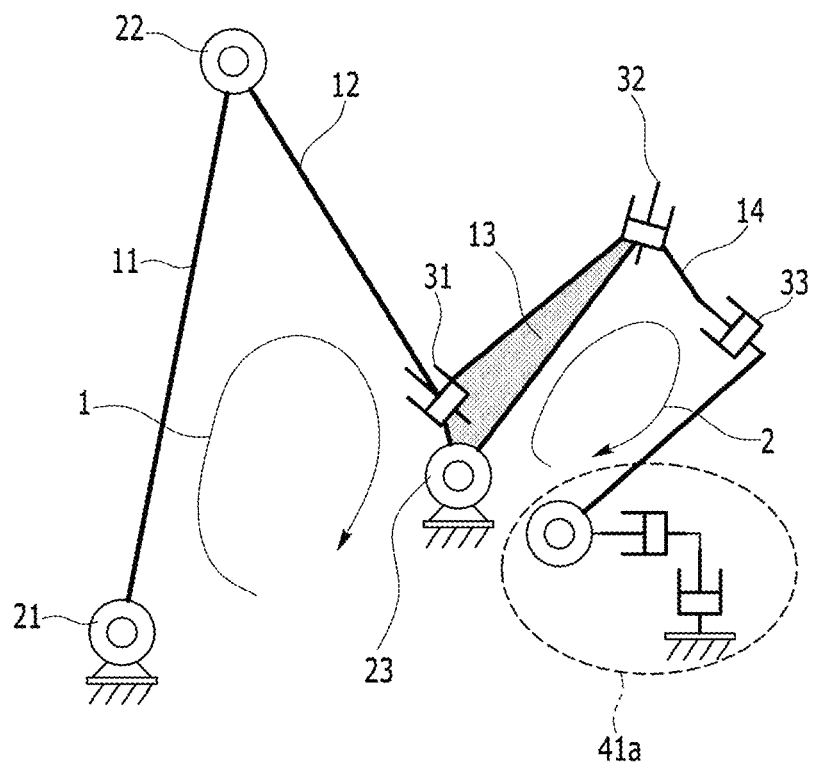
FIG. 2 is a diagram illustrating a connection relationship of the knee joint guide apparatus according to an exemplary embodiment of the present disclosure.

FIG. 2 is a diagram illustrating a connection relationship of the knee joint guide apparatus according to an exemplary embodiment of the present disclosure.

In FIG. 2, virtual revolute and prismatic joints 41a including two links and three joints connected to the third prismatic joint 33 shows an instantaneous center of a different knee joint for each person. That is, the virtual revolute and prismatic joints 41a are a joint for expressing the location of a revolute motion of the knee joint which is fixed and extended. In the virtual revolute and prismatic joints 41a, two orthogonal prismatic joints are joints for representing a center of the knee joint which may be freely positioned in a predetermined space on a plane. That is, in order to express the center of the knee joint of one wearer, two prismatic joints determine a central location of the knee joint according to a slide length, and one revolute joint determines the flexion angle of the knee joint according to a rotation angle.

Therefore, it is shown that the third prismatic joint 33 is connected to the virtual revolute and prismatic joints 41a in FIG. 2, but the third prismatic joint 33 may be attached to the distal body link 15. Here, the distal body link 15 may refer to a shin part below a knee of an actual person. For reference, the proximal body link 10 may refer to a femoral region part above the knee of the actual person.

The proximal body link 10, the third revolute joint 23, the third link 13, the second prismatic joint 32, the fourth joint 14, the third prismatic joint 33, the virtual revolute and prismatic joints 41a, and the proximal body link 10 are connected in sequence to form a second closed loop 2. When the second closed loop 2 has three degrees of freedom before being worn by the wearer, but is worn on the knee joint of one wearer, the virtual revolute and prismatic joints 41a are changed to a joint having one degree of freedom, and as a result, a wearing unit including a mechanism and the knee joint of the wearer generally becomes a one degree-of-freedom system as a whole. That is, once a location ($x_{knee}$, $y_{knee}$) of the knee joint and a flexion angle ($\theta_{knee}$) of the knee joint are determined, movements of another link and joint constituting the second closed loop 2 may also be determined.

The virtual revolute and prismatic joints 41a representing the center of the knee joint are first connected to the fourth link 14 through the third prismatic joint 33. The third prismatic joint 33 which is restrained by the rotation of the knee joint performs a translational movement. The translational movement of the third prismatic joint 33 makes the translational movement of the second prismatic joint 32 through the fourth link 14. Therefore, the third revolute joint 23 attached to the proximal body link 10 makes a rotational movement.

Meanwhile, a first closed loop 1 different from the second closed loop 2 is formed by a sequential connection of the proximal body link 10, the first revolute joint 21, the first link 11, the second revolute joint 22, the second link 12, the first prismatic joint 31, the third link 13, the third revolute joint 23, and the proximal body link 10. In this case, the first revolute joint 21 and the third revolute joint 23 are connected to the proximal body link 10. The actuating unit may be applied to the first revolute joint 21. Since the third link 13 is a link to which the first prismatic joint 31, the third revolute joint 23, and the second prismatic joint 32 are attached jointly, the movement of the first prismatic joint 31 may also be determined when the movement of the third link 13 is determined according to the rotation of the knee joint. When the first prismatic joint 31 performs the translational movement, the second link 12 performs the translational movement parallel thereto. Accordingly, the restrained second revolute joint 22 performs the rotational movement, and lastly, the movement of the first link 11 which is an actuating unit joint is made.

In this case, since the first closed loop 1 has the one degree of freedom in itself, the first closed loop 1 has the same movement according to the flexion angle regardless of the location of the knee joint. Further, the third link 13 as a ternary link connects the first closed loop 1 and the second closed loop 2.

Figure 3:
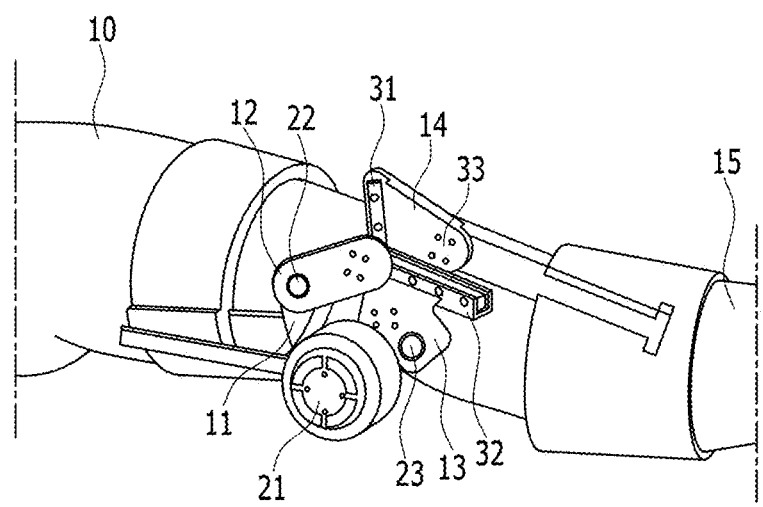
FIG. 3 is a diagram illustrating a state is assumed in which the knee joint guide apparatus is worn by a wearer according to an exemplary embodiment of the present disclosure.
Figure 4:
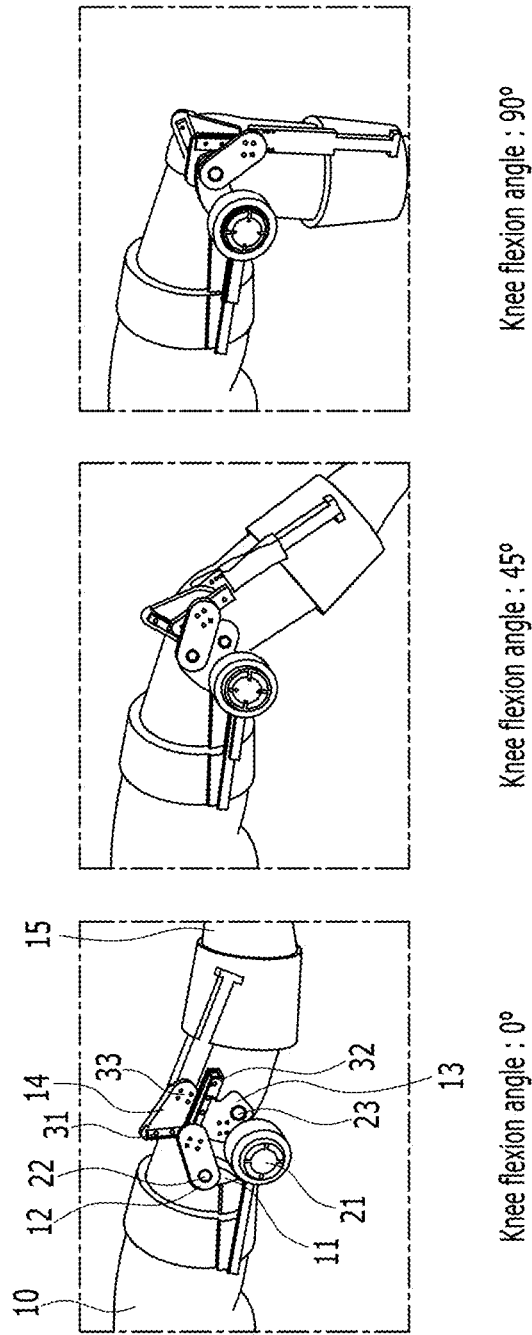
FIG. 4 is a diagram illustrating a state is assumed in which the knee joint guide apparatus is worn by the wearer and moved at a set flexion angle according to an exemplary embodiment of the present disclosure.

FIG. 3 is a diagram assuming and illustrating a state in which the knee joint guide apparatus is worn by a wearer according to an exemplary embodiment of the present disclosure and FIG. 4 is a diagram assuming and illustrating a state in which the knee joint guide apparatus is worn by the wearer and moved at a set flexion angle according to an exemplary embodiment of the present disclosure.

Referring to FIGS. 3 and 4, the movement when the knee joint guide apparatus according to the exemplary embodiment has locations and angles of multiple output units may be known. In the knee joint guide apparatus according to the exemplary embodiment, the knee joint may be positioned at any point in an internal part of at least 30 mm in each of an anterior/posterior direction and a proximal/distal direction on a sagittal plane. Further, the knee joint guide apparatus may have a flexion angle of the knee joint of 0 to 180 degrees.

In FIGS. 3 and 4, a situation is assumed in which the proximal body link 10 and the distal body link 15 are the same as the femoral region and the shin of one wearer. When it is assumed that the proximal body link 10 is a ground, a movement of the distal body link 15 relative to the proximal body link 10 may be defined according to the knee joint movement of the wearer. The knee joint movement of the wearer is implemented by the virtual revolute and prismatic joints 41a. Since the knee joint movement of the wearer is determined, an entire degree of freedom between the knee joint guide apparatus and the wearer according to the exemplary embodiment may form the one degree of freedom system. That is, as the first revolute joint 21 applied as the actuating unit has the rotational movement, the movements of the first link 11 to the fourth link 14 and the second revolute joint 22, the third revolute joint 23, and the first prismatic joint 31 to the third prismatic joint 33 are determined.

In the second closed loop 2, the second prismatic joint 32 and the third prismatic joint 33 correct the knee joint location of the wearer and when the third revolute joint 23 revolves according to the knee joint flexion angle of the wearer, the third revolute joint 23 transmits the movement to multiple joints of the first closed loop 1.

Figure 5:
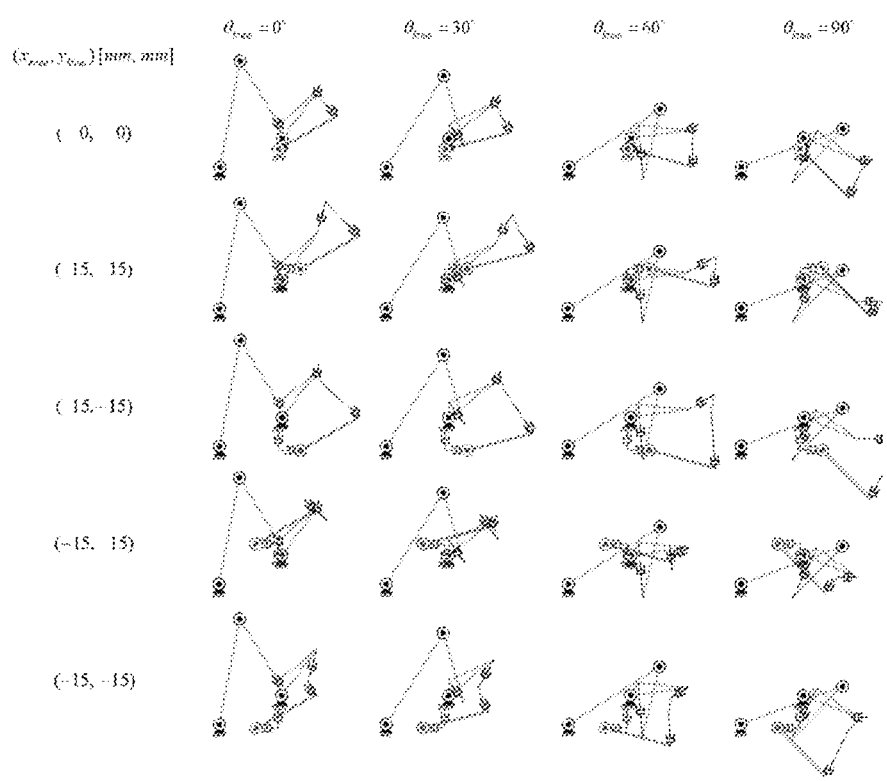
FIG. 5 is a diagram illustrating a mechanism shape change depending on location of a knee joint instant center of rotation and a flexion angle of the knee joint guide apparatus according to an exemplary embodiment of the present disclosure.

FIG. 5 is a diagram illustrating a mechanism shape change depending on a knee joint rotation center location and a flexion angle of the knee joint guide apparatus according to an exemplary embodiment of the present disclosure.

Referring to FIG. 5, a location of a knee joint instant center or rotation is represented by a location of virtual revolute and prismatic joints inside a region indicated by reference numeral 41a in FIG. 2. Knee joints of various wearers may be variously positioned in a predetermined space (inside anterior/posterior direction 30 mm length and proximal/distal direction 30 mm length on the sagittal plane). The location of knee joint instantaneous center of rotation of the wearer is expressed as two orthogonal virtual prismatic joints inside the region indicated by reference numeral 41a in FIG. 2. In this case, the location of the instantaneous center of the knee joint is represented by ($x_{knee}$, $y_{knee}$) and the flexion angle is represented by $\theta_{knee}$. FIG. 5 illustrates a mechanism state when the flexion angle of the knee joint is 0, 30, 60, and 90 degrees when the instantaneous center of the knee joint is positioned at a total of five points.

When a part corresponding to the second closed loop 2 is described, translation movement lengths of the second prismatic joint 32 and the third prismatic joint 33 vary depending on the location of the knee joint. However, the rotation angle of the third revolute joint 23 according to the flexion angle of the knee joint is the same regardless of the location of the instantaneous rotation center of the knee joint.

When a part corresponding to the first closed loop 1 is described, the corresponding part has the same movement according to the flexion angle regardless of the location of the knee joint.

Figure 6A:
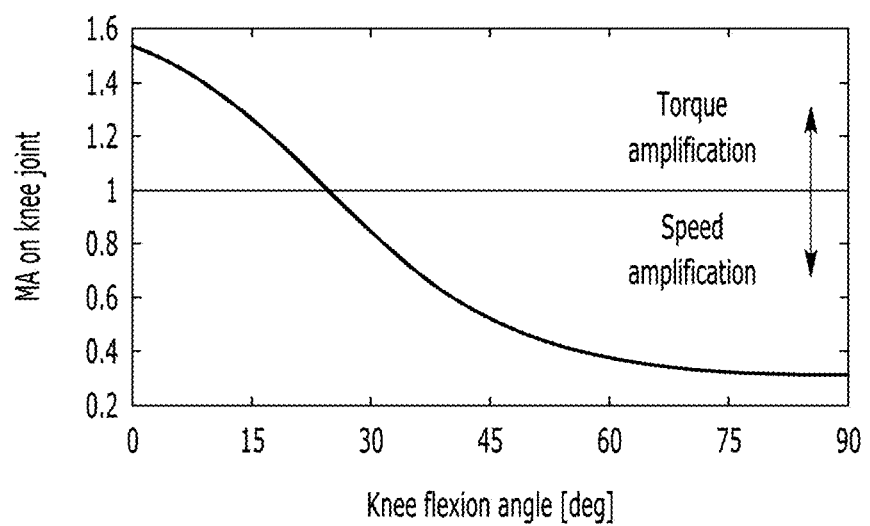
FIG. 6A is a diagram illustrating a mechanical advantage according to the flexion angle of a knee joint.
Figure 6B:
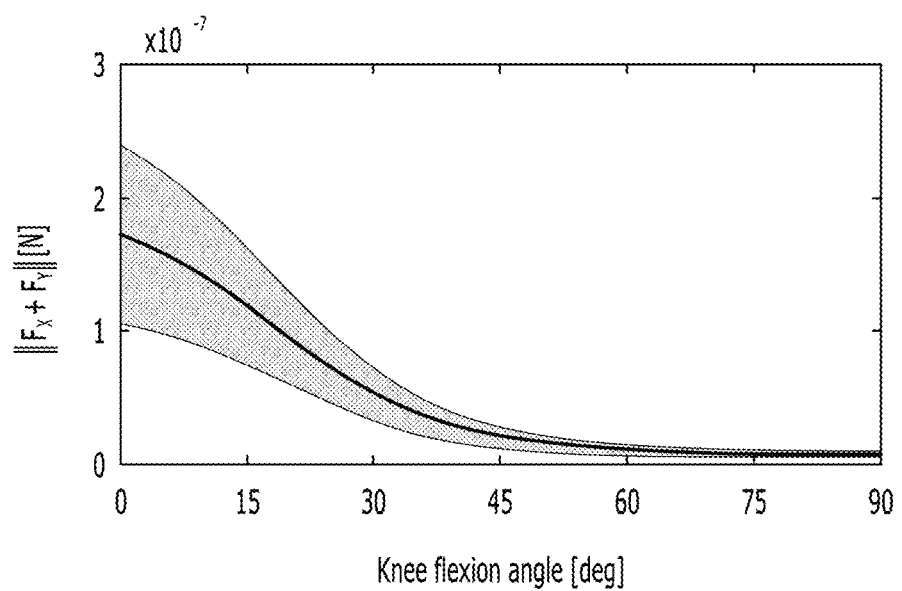
FIG. 6B is a diagram illustrating a size of shear force depending on the flexion angle of the knee joint.

FIG. 6A is a graph illustrating a mechanical advantage according to the flexion angle of the knee joint in the knee joint guide apparatus according to an exemplary embodiment and FIG. 6B is a graph illustrating a size of shear force depending on the flexion angle of the knee joint.

When the flexion angle is 0 degree or more and approximately 20 degrees or less, the mechanical advantage is 1 or more and a torque of the actuating unit may be increased and transmitted in the output unit. When the flexion angle is approximately 20 degrees or more, the mechanical advantage is 1 or less and an angular velocity of the actuating unit may be increased and transmitted in the output unit. A maximum torque which the actuating unit should assist for the walking operation through the change in mechanical advantage depending on the angle is smaller than that of a robot of a simple revolute joint. Further, there is little unnecessary shear force applied to the body regardless of the knee joint location on the sagittal plane at all angles. That is, the knee joint guide apparatus according to the exemplary embodiment may possess the self-alignment function in a working space of the sagittal plane.

Figure 7A:
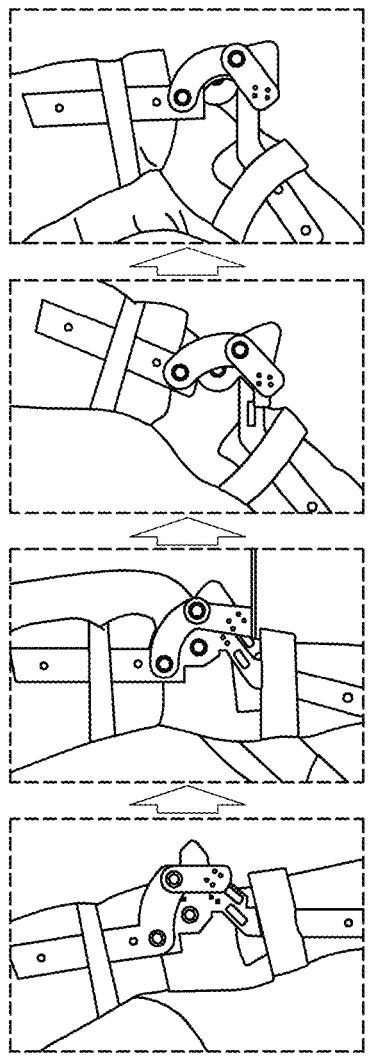
FIGS. 7A and 7B are diagrams illustrating a state in which a proto type of the knee joint guide apparatus is worn according to an exemplary embodiment of the present disclosure.
Figure 7B:
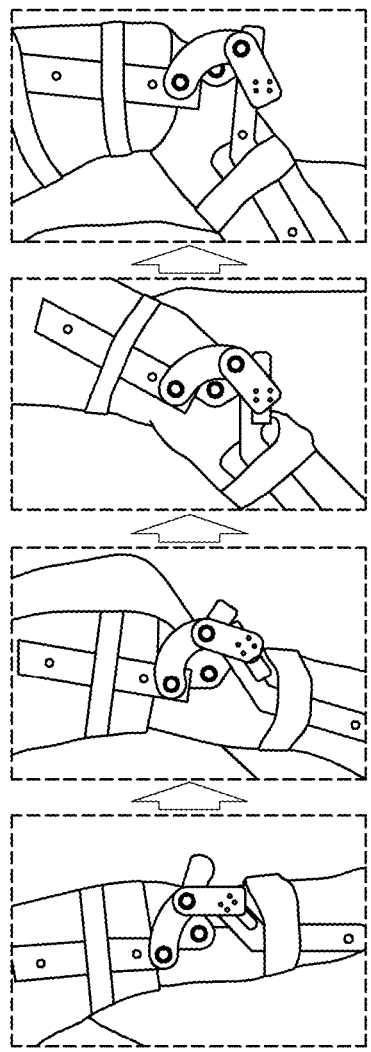

FIGS. 7A and 7B are diagrams illustrating a state in which a proto type of the knee joint guide apparatus is worn according to an exemplary embodiment of the present disclosure. FIG. 7A is a diagram illustrating a state in which a woman having a height of an early range of 160 cm wears the proto type of the knee joint guide apparatus according to the exemplary embodiment of the present disclosure. In addition, FIG. 7B is a diagram illustrating a state in which a man having a height of a middle range of 170 cm wears the proto type of the knee joint guide apparatus according to the exemplary embodiment of the present disclosure.

Referring to FIGS. 7A and 7B, it can be seen that even though different persons wear the same proto type, the walking operation is not difficult.

While this disclosure has been described in connection with what is presently considered to be practical exemplary embodiments, it is to be understood that the disclosure is not limited to the disclosed embodiments. On the contrary, it is intended to cover various modifications and equivalent arrangements included within the spirit and scope of the appended claims.

<Description of symbols>

| | |
|---|---|
| 10; Proximal body link | 11; First link |
| 12; Second link | 13; Third link |
| 14; Fourth link | 15; Distal body link |
| 21; First revolute joint | 22; Second revolute joint |
| 23; Third revolute joint | 31; First prismatic joint |
| 32; Second prismatic joint | 33; Third prismatic joint |

What is claimed is:

1. A knee joint guide apparatus comprising:
a proximal body link configured to be provided above a knee joint;
a distal body link configured to be provided at a location corresponding to the proximal body link below the knee joint; and
a planar rigid body 6-bar linkage mechanism including a plurality of revolute joints and a plurality of prismatic joints, and a plurality of links between the proximal body link and the distal body link configured to output a mechanical advantage depending on a flexion angle of the knee joint in movement of the knee joint with a self-alignment function.

2. The knee joint guide apparatus of claim 1, wherein:
the proximal body link, the distal body link, and the planar rigid body 6-bar linkage mechanism form one closed loop and have one degree of freedom.

3. The knee joint guide apparatus of claim 2, wherein:
the planar rigid body 6-bar linkage mechanism
includes three revolute joints, three prismatic joints, and four links.

4. The knee joint guide apparatus of claim 3, wherein:
the three revolute joints include
a first revolute joint connecting the proximal body link and a first link,
a second revolute joint connecting the first link and a second link, and
a third revolute joint connecting the proximal body link and a third link.

5. The knee joint guide apparatus of claim 4, wherein:
the three prismatic joints include
a first prismatic joint connecting the second link and the third link,
a second prismatic joint connecting the third link and a fourth link, and
a third prismatic joint connecting the fourth link and the distal body link.

6. The knee joint guide apparatus of claim 5, wherein:
the first prismatic joint, the third revolute joint, and the second prismatic joint are connected to each other through the third link.

7. The knee joint guide apparatus of claim 6, wherein: the first revolute joint is connected to a first end of the proximal body link, a first end of the first link is connected to the first revolute joint, the second revolute joint is connected to a second end of the first link, a first end of the second link is connected to the second revolute joint, the first prismatic joint is connected to a second end of the second link, a first end of the third link is connected to the first prismatic joint, and the third revolute joint is connected to the third link to form a first closed loop.

8. The knee joint guide apparatus of claim 7, wherein: the third revolute joint is connected to a second end of the proximal body link, a second end of the third link is connected to the third revolute joint, the second prismatic joint is connected to the first end of the third link, a first end of the fourth link is connected to the second prismatic joint, and the third prismatic joint is connected to a second end of the fourth link to form a second closed loop.

9. The knee joint guide apparatus of claim 4, wherein:
the first revolute joint further includes an actuating unit generating actuating torque.

10. The knee joint guide apparatus of claim 3, wherein:
the four links include at least one ternary link.

* * * * *